United States Patent
Weber et al.

(10) Patent No.: US 11,839,500 B2
(45) Date of Patent: Dec. 12, 2023

(54) METHOD FOR ACQUIRING AN X-RAY IMAGE SECTION BY SECTION

(71) Applicant: Siemens Healthcare GmbH, Erlangen (DE)

(72) Inventors: Thomas Weber, Hausen (DE); Christoph Luckner, Erlangen (DE); Magdalena Herbst, Pinzberg (DE); Ludwig Ritschl, Buttenheim (DE); Frank Boettcher, Ortspitz (DE)

(73) Assignee: Siemens Healthcare GmbH, Erlangen (DE)

( * ) Notice: Subject to any disclaimer, the term of this patent is extended or adjusted under 35 U.S.C. 154(b) by 153 days.

(21) Appl. No.: 17/386,198

(22) Filed: Jul. 27, 2021

(65) Prior Publication Data
US 2022/0031260 A1    Feb. 3, 2022

(30) Foreign Application Priority Data

Jul. 31, 2020   (DE) .................... 10 2020 209 714.3

(51) Int. Cl.
*A61B 6/02*   (2006.01)
*A61B 6/04*   (2006.01)
*A61B 6/00*   (2006.01)

(52) U.S. Cl.
CPC ............ *A61B 6/027* (2013.01); *A61B 6/0407* (2013.01); *A61B 6/4417* (2013.01); *A61B 6/5211* (2013.01); *A61B 6/025* (2013.01)

(58) Field of Classification Search
CPC ....... A61B 6/025; A61B 6/027; A61B 6/0407; A61B 6/0487; A61B 6/4417; A61B 6/5211
See application file for complete search history.

(56) References Cited

U.S. PATENT DOCUMENTS 9,055,913 B2 *   6/2015   Manak ................... A61B 6/027
9,427,205 B1 *   8/2016   Chen ........................ A61B 6/56
(Continued)

FOREIGN PATENT DOCUMENTS

DE   102016205176 A1   10/2017
DE   102018212389 B3   1/2020
JP     2011019801 A  *  2/2011

OTHER PUBLICATIONS

Machine translation JP-2011019801 (Year: 2011).*
(Continued)

*Primary Examiner* — Dani Fox
*Assistant Examiner* — Soorena Kefayati
(74) *Attorney, Agent, or Firm* — Harness, Dickey & Pierce, P.L.C.

(57) ABSTRACT

A method is for acquiring an X-ray image of a region of interest of an examinee using an X-ray system and a displaceable patient table for positioning the examinee. In an embodiment, the method includes: selecting the region of interest; acquiring, section-by-section, successive image sections in relation to the region of interest, the acquiring, for each successive image section of the successive image sections, including moving the X-ray source and the X-ray detector along a common acquisition direction, moving the patient table counter to the common acquisition direction, determining a respective essentially strip-shaped detection area within the detection zone for a respective image section of the successive image sections, and detecting the respective image section by way of the determined detection area and the X-ray source, to acquire the respective image section; and generating a composite X-ray image of the region of interest from the respective successive image sections.

18 Claims, 3 Drawing Sheets

(56) References Cited

U.S. PATENT DOCUMENTS

| | | | |
|---|---|---|---|
| 10,729,394 B1* | 8/2020 | Foos | A61B 6/06 |
| 2004/0114717 A1* | 6/2004 | Kato | A61B 6/5241 |
| | | | 378/197 |
| 2010/0189214 A1* | 7/2010 | Shibata | A61B 6/027 |
| | | | 378/21 |
| 2011/0033024 A1* | 2/2011 | Dafni | A61B 6/027 |
| | | | 378/11 |
| 2011/0206185 A1* | 8/2011 | Sakai | A61B 6/06 |
| | | | 378/62 |
| 2012/0002790 A1* | 1/2012 | Tanaka | A61B 6/025 |
| | | | 378/198 |
| 2012/0027166 A1* | 2/2012 | Akahori | A61B 6/025 |
| | | | 378/19 |
| 2012/0128119 A1* | 5/2012 | Notohara | A61B 6/025 |
| | | | 378/10 |
| 2012/0236992 A1* | 9/2012 | Engel | A61B 6/484 |
| | | | 977/939 |
| 2013/0108018 A1* | 5/2013 | Takamura | A61B 6/505 |
| | | | 378/42 |
| 2013/0148779 A1* | 6/2013 | Notohara | A61B 6/025 |
| | | | 378/22 |
| 2013/0287168 A1* | 10/2013 | Payne | A61B 6/5205 |
| | | | 378/53 |
| 2014/0254753 A1* | 9/2014 | Yamashita | A61B 6/06 |
| | | | 378/62 |
| 2015/0146851 A1* | 5/2015 | Wilson | A61B 6/505 |
| | | | 378/62 |
| 2015/0250441 A1* | 9/2015 | Okuno | A61B 6/547 |
| | | | 378/62 |
| 2016/0074004 A1* | 3/2016 | Braun | G06F 3/017 |
| | | | 378/205 |
| 2016/0113601 A1* | 4/2016 | Notohara | A61B 6/5205 |
| | | | 378/7 |
| 2016/0174930 A1* | 6/2016 | Braun | A61B 6/0407 |
| | | | 378/205 |
| 2016/0228086 A1* | 8/2016 | Toyoda | A61B 6/463 |
| 2017/0135658 A1* | 5/2017 | Saito | A61B 6/5235 |
| 2017/0281109 A1* | 10/2017 | Ecabert | A61B 6/545 |
| 2017/0325773 A1* | 11/2017 | Nishino | A61B 6/542 |
| 2018/0188193 A1* | 7/2018 | Toyoda | A61B 6/487 |
| 2018/0284594 A1* | 10/2018 | Gao | A61B 6/0487 |
| 2018/0296177 A1* | 10/2018 | Chang | A61B 6/08 |
| 2019/0142356 A1* | 5/2019 | Nakaya | A61B 6/00 |
| | | | 378/98.8 |
| 2019/0261939 A1* | 8/2019 | Yoshida | A61B 6/547 |
| 2020/0029916 A1 | 1/2020 | Fieselmann et al. | |
| 2020/0305813 A1* | 10/2020 | Yoshida | A61B 6/54 |
| 2021/0153825 A1* | 5/2021 | Shizukuishi | A61B 6/4241 |
| 2021/0298699 A1 | 9/2021 | Herbst et al. | |
| 2021/0345943 A1* | 11/2021 | Nakaya | A61B 6/4233 |

OTHER PUBLICATIONS

Translation of JP-2011019801-A (Year: 2011).*
German Office Action for German Application No. 10 2020 209 714.3 dated Apr. 20, 2021.

* cited by examiner

METHOD FOR ACQUIRING AN X-RAY IMAGE SECTION BY SECTION

PRIORITY STATEMENT

The present application hereby claims priority under 35 U.S.C. § 119 to German patent application number DE 102020209714.3 filed Jul. 31, 2020, the entire contents of which are hereby incorporated herein by reference.

FIELD

Example embodiments of the invention generally relate to a method for acquiring an X-ray image section by section and to a medical X-ray system, a computer program product and a computer-readable medium therefor.

BACKGROUND

By way of radiography and in particular also in fluoroscopy, two- and three-dimensional X-ray images of an examinee can be acquired. The examinee is disposed between an X-ray source and an X-ray detector, wherein the X-ray source emits X-rays and the X-ray detector receives the X-rays which have passed through the examinee.

In the event that, for an X-ray image, the area to be acquired, i.e. the region of interest, is larger than the detectable area or rather the detection zone of the X-ray detector, a plurality of images are generally acquired in succession using the entire detection zone and then joined together. In this way, long images can be produced in one dimension. This method is used, for example, for orthopedic images. However, these images are acquired with a wide collimation, i.e. the X-ray radiation is incident on the entire detection zone as a widely flared cone. As a result, the individual partial images are subject, toward the edge, to varying magnification in respect of the region of interest.

The inventors have recognized that another option is to move the examinee (patient) on a tabletop or patient positioning table relative to the X-ray detector and X-ray source. However, at fast speeds, e.g. more than 10 cm/s, this is unpleasant for the patient.

The publication DE 10 2018 212 389 B3 discloses a method for operating an X-ray device, wherein a sequence of images of a patient is acquired and an acquisition arrangement comprising at least one X-ray emitter moves along the patient in a scan direction during acquisition of the sequence of images. By evaluating at least two different images showing the same feature of the patient, depth information is determined for at least one of these features, wherein, depending on position information describing the position of the acquisition arrangement in the scanning direction, a collimator aperture of a collimator of the X-ray source is controlled to change an aperture angle of a radiation field generated by the X-ray source in the scanning direction.

SUMMARY

Embodiments of the invention specify a method for acquiring an X-ray image, a medical X-ray system, a computer program product and a computer-readable medium, which allow distortion-free radiographic imaging, in particular sectional X-ray acquisition, at least along the acquisition direction, using an X-ray system having a limited travel range of the X-ray source or the X-ray detector.

Embodiments of the invention are directed to a method for acquiring an X-ray image, a medical X-ray system, a computer program product, and a computer-readable medium.

At least one embodiment of the invention relates to a method for acquiring an X-ray image of a region of interest of an examinee using an X-ray system. The X-ray system comprises an X-ray source disposed on a traversing unit and an X-ray detector having a detection zone disposed on the traversing unit. The X-ray system further comprises a displaceable patient table for positioning the examinee. The method comprises the steps of selection, section-by-section acquisition, and generation. In the selecting step, the region to be examined is selected. In the section-by-section acquisition step, successive image sections are acquired in respect of the region of interest. The section-by-section acquisition step comprises the step of moving the X-ray source and X-ray detector along a common acquisition direction and the step of moving the patient table counter to the acquisition direction. The section-by-section acquisition step further comprises the step of determining an essentially strip-shaped detection area within the detection zone for the image section and the step of detecting the image section by way of the determined detection area and the X-ray source. In the generating step, a composite X-ray image of the region of interest is generated from the image sections.

At least one embodiment of the invention further relates to a medical X-ray system for carrying out a method according to at least one embodiment of the invention. The X-ray system can in particular be designed as a radiography or fluoroscopy system. The X-ray source and the X-ray detector can preferably be mechanically interconnected and moved together along an acquisition direction. The X-ray source and the X-ray detector can preferably be enclosed by a common traversing unit. The X-ray system can also comprise a selection unit for selecting the region of interest. The X-ray system can comprise an acquisition unit for section-by-section acquisition. The acquisition unit can incorporate the traversing unit. The acquisition unit can comprise a movement i.e. traversing unit for moving the X-ray detector and the X-ray source. The acquisition unit can comprise the X-ray detector and the X-ray source. The acquisition unit can further comprise a determination unit for determining the essentially strip-shaped detection area. The acquisition unit can comprise a detection unit for detecting the image section. The X-ray system can further comprise a generating unit for generating a composite X-ray image. By way of the method according to the invention, the region of interest, in particular the maximum possible region under examination, can be advantageously enlarged.

At least one embodiment of the invention further relates to a computer program product comprising a computer program which can be loaded directly into a memory device of a control device of an X-ray system and having program sections for carrying out all the steps of a method according to at least one embodiment of the invention when the computer program is executed in the control device of the X-ray system. The method according to at least one embodiment of the invention can advantageously be carried out in an automated manner.

At least one embodiment of the invention further relates to a computer-readable medium on which are stored program sections readable and executable by a computer unit in order to carry out all the steps of a method according to at least one embodiment of the invention when the program sections are executed by the X-ray system.

At least one embodiment of the invention further relates to a method for acquiring an X-ray image of a region of interest of an examinee using an X-ray system including an X-ray source disposed on a traversing unit and an X-ray detector including a detection zone disposed on the traversing unit, and including a displaceable patient table to position the examinee, the method comprising:

selecting the region of interest;
acquiring, section-by-section, successive image sections in relation to the region of interest, the acquiring, for each successive image section of the successive image sections, including
moving the X-ray source and the X-ray detector along a common acquisition direction,
moving the patient table counter to the common acquisition direction,
determining a respective essentially strip-shaped detection area within the detection zone for a respective image section of the successive image sections, and
detecting the respective image section by way of the determined detection area and the X-ray source, to acquire the respective image section; and
generating a composite X-ray image of the region of interest from the respective successive image sections.

At least one embodiment of the invention further relates to a medical X-ray system, comprising:

at least one processor method for acquiring an X-ray image of a region of interest of an examinee using an X-ray system including an X-ray source disposed on a traversing unit and an X-ray detector including a detection zone disposed on the traversing unit, and including a displaceable patient table to position the examinee, the method comprising:
selecting the region of interest;
acquiring, section-by-section, successive image sections in relation to the region of interest, the acquiring, for each successive image section of the successive image sections, including
moving the X-ray source and the X-ray detector along a common acquisition direction,
moving the patient table counter to the common acquisition direction,
determining a respective essentially strip-shaped detection area within the detection zone for a respective image section of the successive image sections, and
detecting the respective image section by way of the determined detection area and the X-ray source, to acquire the respective image section; and
generating a composite X-ray image of the region of interest from the respective successive image sections.

At least one embodiment of the invention further relates to a non-transitory computer program product storing a computer program, directly loadable into a memory device of a control device of an X-ray system, including program sections for performing the method of an embodiment when the computer program is executed in the control device of the X-ray system.

At least one embodiment of the invention further relates to a non-transitory computer-readable medium storing program sections, readable and executable by a computer unit, for performing the method of an embodiment when the program sections are executed by the X-ray system.

BRIEF DESCRIPTION OF THE DRAWINGS

Example embodiments of the invention will now be explained in more detail with reference to the accompanying drawings in which.

DETAILED DESCRIPTION OF THE EXAMPLE EMBODIMENTS

Figure 1:
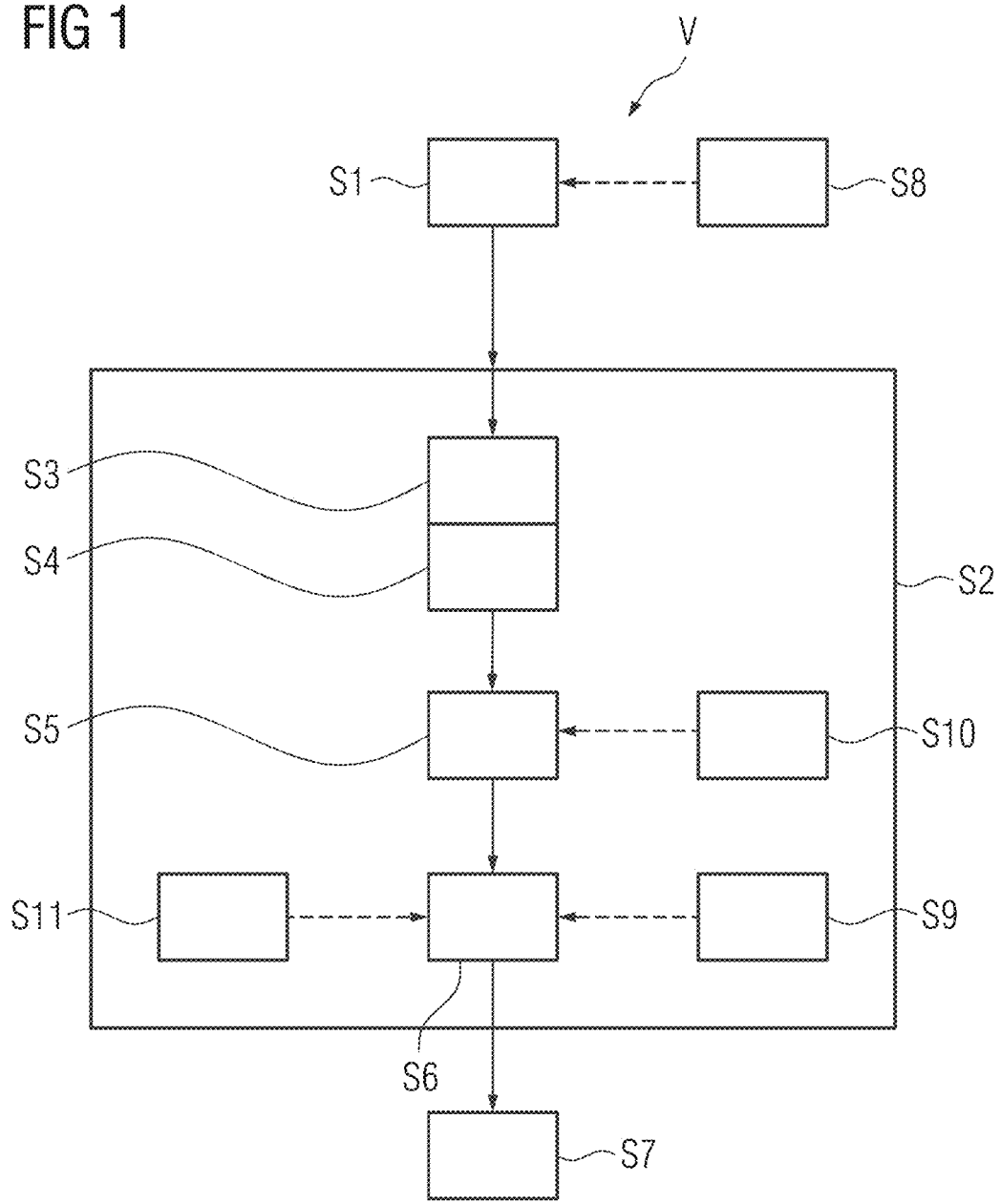
FIG. 1 schematically illustrates a method according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for acquiring an X-ray image of a region of interest of an examinee using an X-ray system. The X-ray system comprises an X-ray source disposed on a traversing unit and an X-ray detector having a detection zone disposed on the traversing unit. The X-ray system further comprises a displaceable patient table for positioning the examinee. The method comprises the steps of selection, section-by-section acquisition, and generation. In the selecting step, the region to be examined is selected. In the section-by-section acquisition step, successive image sections are acquired in respect of the region of interest. The section-by-section acquisition step comprises the step of moving the X-ray source and X-ray detector along a common acquisition direction and the step of moving the patient table counter to the acquisition direction. The section-by-section acquisition step further comprises the step of determining an essentially strip-shaped detection area within the detection zone for the image section and the step of detecting the image section by way of the determined detection area and the X-ray source. In the generating step, a composite X-ray image of the region of interest is generated from the image sections.

In particular, an embodiment of the method relates to X-ray image acquisition using a radiography or fluoroscopy system. The X-ray source and the X-ray detector can in particular be mechanically interconnected so that both can be moved together in the acquisition direction by a common traversing unit. In addition, the X-ray detector can, for example, be displaced relative to the X-ray source using an additional traversing unit within the X-ray source/X-ray detector unit. For example, the X-ray detector can be rotatably mounted so that it can be rotated about the surface normal. The patient table for positioning the examination object can also be termed a tabletop. The patient table can in particular be mechanically independent of the X-ray detector. The patient table can in particular be movable independently of the X-ray detector. The examinee can in particular be disposed on the patient table between the X-ray source and the X-ray detector. The examinee can be in particular a patient. The method can be carried out both with the patient in a recumbent position and with the patient standing up. In the case of a fluoroscopy system, for example, the patient can be positioned standing on the footrest of the system. In particular, the examinee can be disposed in a recumbent or standing position in the X-ray system using the patient table, in which case the longitudinal axis of the patient is usually aligned parallel to the length of the patient table. The longitudinal axis of the patient can preferably be aligned parallel to the acquisition direction.

Alternatively, the radiography system comprises an X-ray source disposed on a first traversing unit and an X-ray detector having a detection zone disposed on a second traversing unit different from the first. This can be termed a robotic radiography system. The alternative radiography system further comprises a displaceable patient table for positioning the examinee.

Acquisition of the X-ray image is in particular carried out section by section. In particular, the method includes acquiring a plurality of in particular at least partially overlapping image sections. The X-ray source can move together with the X-ray detector over a short distance in the acquisition direction, while the patient table moves in particular the same short distance in the opposite direction. A first section of the image is acquired. The movement steps are then repeated and a subsequent, second image section is acquired.

In the selection step, the region of interest is selected manually or preferably automatically. The region of interest can be based, for example, on a type of examination or an organ program. For example, an examination type can be a body region specification such as whole body, trunk or leg.

In the determining step, an essentially or in particular strip-shaped detection area is determined within the detection zone for the image section. The strip-shaped area can be selected at least a factor of 4 smaller than the detection zone. For example, the strip-shaped area can extend along the entire width of the detection zone perpendicular to the acquisition direction. The strip-shaped detection area can have an extent or more specifically a height of e.g. between 2 and 8 cm, preferably approximately 5 cm, along the acquisition direction. The width of the detection area can be at least a factor of 2 greater than the height of the detection area. The extent of the detection area can be determined in particular by collimation of the X-ray beam. For this purpose, the X-ray beam can be collimated via collimator apertures close to the X-ray source. As will be explained later, the detection area can be extended, for example, for some of the image sections along the acquisition direction. In the detecting step, the image section is detected by way of the determined detection area and the X-ray source.

In the generating step, a composite X-ray image of the region of interest is generated from the image sections. The composite X-ray image can be generated in particular by tomosynthesis reconstruction or by using back projection based on image data sets of the image sections. The image sections or rather their image data sets can preferably overlap, so that a point in the region of interest is covered by a plurality of image sections. Alternatively, the image sections can be assembled into an X-ray image using a stitching algorithm.

A distortion-free picture can be generated as a composite X-ray image by tomosynthesis reconstruction from a plurality of individual acquisitions or rather image sections. The image sections can be tightly collimated in the acquisition direction, e.g. approximately 5 cm, in order to suppress scattered radiation. This is possible because depth resolution is not necessary for this type of imaging, or may only be necessary in some sections.

The common travel range of the X-ray source and X-ray detector may be limited to about 113 cm in current fluoroscopy equipment. Pure table movement may be possible up to a travel distance of 160 cm, but is often impractical because of the room situation, especially when the device is upright or the patient table is upright in order to position a standing patient because of insufficient ceiling height, and the speed problem. The inventors have recognized that statistically only some of the population are able to be examined in this way.

The movement of the X-ray source and the X-ray detector relative to the patient table advantageously enables the acquisition area, i.e. the region of interest, to be extended beyond that of the individual components. This advantageously means that even very tall patients can be examined for whom the travel range of the single axis of X-ray source, X-ray detector and/or patient table would be insufficient. Despite an advantageously high relative speed, the tabletop or patient table can move comparatively slowly, which advantageously reduces the likelihood of motion artefacts. Tomosynthesis reconstruction in conjunction with the parallel displacement of a tightly collimated scan area can provide freedom from distortion in the acquisition direction.

According to an embodiment of the invention, movement of the X-ray source and X-ray detector and movement of the patient table occur essentially simultaneously. Synchronous movement of the X-ray source/X-ray detector unit and patient table advantageously allows both a high relative speed between the components and an extended acquisition range. In addition, the speed of the tabletop or patient table is comparatively low, which reduces the likelihood of motion artefacts, while the relative speed is nevertheless comparatively high in order to achieve a low total acquisition time.

By way of example, the X-ray image can be acquired as follows, preferably in the order stated. First, the X-ray system can be prepared so that the central beam of the X-ray source runs along the surface normal of the X-ray detector. A maximum distance between the X-ray detector and the X-ray source can be selected. A minimum distance between the patient table and the X-ray detector can be selected. The user can select an examination mode. The patient is positioned standing or recumbent. The patient can be positioned in a.p., p.a. or laterally. In a standing position, the patient can also be positioned on a footrest. A start and a stop position of the region of interest can be determined, e.g. via a light field, a laser line or a camera image. X-ray acquisition can then be performed section by section. The patient can leave the patient table as soon as a preview image has been checked, so that no repetition of the X-ray acquisition is necessary. The X-ray image can be generated.

The relative speed between the X-ray source/X-ray detector unit and the patient table can be e.g. between 200 and 300 mm/s, preferably 270 mm/s. An examination range of up to 178 cm can preferably be provided, wherein the X-ray source/X-ray detector unit can move e.g. 113 cm. The speed of the X-ray source/X-ray detector unit can be e.g. approximately 17.1 cm/s. The speed of the patient table can be e.g. approximately 9.9 cm/s.

According to an embodiment of the invention, a camera unit is used to determine a start position and/or a stop position of the region of interest. The start position and/or the stop position can be an upper and lower limit respectively of the region of interest, spaced along the acquisition direction. The start position and/or the stop position can be determined automatically or manually. A camera system or a camera unit can be used to automate the calibration, i.e. the finding or determining of the start and stop position. Advantageously, the region of interest can be individually matched to the patient. The camera unit can in particular be designed as a two- or three-dimensional camera unit. In particular, the camera unit can be disposed on the X-ray source, e.g. on an outer lateral surface of the collimator. Alternatively, the camera unit can be disposed on the X-ray system or in the examination room in such a way that the field of view completely encompasses the patient.

The start position or the stop position can be determined manually e.g. by the start position or the stop position being determined on a display unit, preferably a touch-sensitive screen, i.e. a so-called touchscreen, by a user input on a camera image displayed thereon. The start position or the stop position can be determined semi-manually by a suggestion being displayed on the camera image, e.g. based on recognized landmarks in the camera image, and the user then adjusting the start position or the stop position by an input, in particular by changing a marking on the camera image. Alternatively, the start or stop position can be determined using a light marker on the patient.

According to an embodiment of the invention, at least one landmark of the examinee is automatically pinpointed. Characteristic features, in particular so-called landmarks, can be detected or pinpointed based on the camera image captured by the camera unit. A characteristic feature can be, for example, shoulders, nose or pelvis. The pinpointing of the landmark can be carried out both using an, in particular known, neural network, i.e. artificial intelligence, or using a known image processing method. Advantageously, the region of interest can be optimized for the patient. For example, an examination type can be specified by the user. At least one landmark can be assigned to the examination type. The region of interest can be selected, in particular automatically, based on the landmark pinpointed in the camera image. For example, a predefined distance from a landmark can be used for this purpose. Preferably, a plurality of landmarks can be located and used to select the region of interest for an examination type. The automatic calibration or selection of the region of interest via a camera system or camera unit advantageously reduces user workload.

According to an embodiment of the invention, the landmark is located using a neural network. For example, a so-called skeletal tracker or another known neural network can be used. Selection of the region of interest can be advantageously improved.

According to an embodiment of the invention, a first collimation of the X-ray source perpendicular to the acquisition direction is set, in particular automatically, based on image capture via a camera unit. The first collimation can also be referred to as width collimation. The camera system can also be used to perform automatic (width) collimation, in particular dynamically adjusted during section-by-section acquisition, in order to minimize direct radiation on the X-ray detector. This can be particularly advantageous when examining a patient i.e. taking an X-ray of the region of interest, in lateral orientation. Without this initial collimation, there may be large areas of direct radiation from the X-ray source onto the X-ray detector, particularly in the lateral orientation.

According to an embodiment of the invention, a second collimation of the X-ray source parallel to the acquisition direction is varied between successive image sections. A second collimation can be automatically varied in the acquisition direction to provide depth resolution at specific body regions after reconstruction, i.e. when generating the composite X-ray image. The second collimation can be widened in the acquisition direction, i.e. the flare angle can be increased, in order to obtain depth information for the image section. Advantageously, areas of particular interest, e.g. the knee, can be displayed with a depth resolution in the composite X-ray image or also in a separate display. The adaptive or varied collimation can advantageously provide an optimally adjusted width, especially when performing frontal (a.p.) and lateral acquisition in immediate succession.

According to an embodiment of the invention, dose modulation for lateral X-ray acquisition is determined based on prior frontal X-ray acquisition of the region of interest. The information from a frontal X-ray or so-called frontal topogram scan can be used to calculate dose modulation for lateral acquisition. By projection of the attenuation values, an approximate length profile of the patient's absorption can be determined for a lateral beam path. This allows the dose to be increased in areas of high attenuation and reduced in areas of low attenuation. Dose modulation during lateral acquisition advantageously ensures optimum acquisition at the lowest possible dose exposure for the patient.

According to an embodiment of the invention, the detection area within the detection zone is shifted in the acquisition direction compared to a preceding detection area of a preceding image section. The detection area in a first image section can be formed by a position within the detection zone. The detection area of a subsequent second image section can be formed shifted within the detection zone in the acquisition direction. Advantageously, the possible region under examination can be further enlarged, since e.g. the edge areas of the X-ray detector can also be used in addition to a detection area formed centrally in the detection zone. The radiation load of the X-ray detector can advantageously be made uniform within the detection zone.

According to an embodiment of the invention, the detection area is determined along a diagonal of the detection zone. In particular, the detection area can be rectangular, with preference essentially square. The X-ray detector can be rotatably mounted about the surface normal. The X-ray detector can be rotated in such a way that the diagonal of the detection area is aligned perpendicular to the acquisition direction. The detection area can be formed along the diagonal of the detection zone. Advantageously, the extent or width of the X-ray image perpendicular to the acquisition direction can be advantageously increased.

At least one embodiment of the invention further relates to a medical X-ray system for carrying out a method according to at least one embodiment of the invention. The X-ray system can in particular be designed as a radiography or fluoroscopy system. The X-ray source and the X-ray detector can preferably be mechanically interconnected and moved together along an acquisition direction. The X-ray source and the X-ray detector can preferably be enclosed by a common traversing unit. The X-ray system can also comprise a selection unit for selecting the region of interest. The X-ray system can comprise an acquisition unit for section-by-section acquisition. The acquisition unit can incorporate the traversing unit. The acquisition unit can comprise a movement i.e. traversing unit for moving the X-ray detector and the X-ray source. The acquisition unit can comprise the X-ray detector and the X-ray source. The acquisition unit can further comprise a determination unit for determining the essentially strip-shaped detection area. The acquisition unit can comprise a detection unit for detecting the image section. The X-ray system can further comprise a generating unit for generating a composite X-ray image. By way of the method according to the invention, the region of interest, in particular the maximum possible region under examination, can be advantageously enlarged.

At least one embodiment of the invention further relates to a computer program product comprising a computer program which can be loaded directly into a memory device of a control device of an X-ray system and having program sections for carrying out all the steps of a method according to at least one embodiment of the invention when the computer program is executed in the control device of the X-ray system. The method according to at least one embodiment of the invention can advantageously be carried out in an automated manner.

At least one embodiment of the invention further relates to a computer-readable medium on which are stored program sections readable and executable by a computer unit in order to carry out all the steps of a method according to at least one embodiment of the invention when the program sections are executed by the X-ray system.

FIG. 1 shows an example embodiment of the method V according to the invention for acquiring an X-ray image of a region of interest of an examinee using an X-ray system. The X-ray system comprises an X-ray source disposed on a traversing unit and, also disposed on the traversing unit, an X-ray detector having a detection zone, and a displaceable patient table for positioning the examinee. The method V comprises the steps of selection S1, section-by-section acquisition S2 and generation S7 of the composite X-ray image. The region of interest is selected in selection step S1.

In the section-by-section acquisition step S2, successive image sections are acquired in respect of the region of interest. The section-by-section acquisition step S2 comprises the steps of moving S3, S4, determining S5 and detecting S6.

In the movement step S3, the X-ray source and the X-ray detector are moved along a common acquisition direction. In movement step S4, the patient table is moved in the opposite direction to the acquisition direction. The moving S3 of the X-ray source and X-ray detector as well as the moving S4 of the patient table take place essentially simultaneously. The movement steps S3, S4 are automated, in particular motorized.

In the determining step S5, an essentially strip-shaped detection area within the detection zone is determined for the image section. The detection area can optionally be shifted within the detection zone compared to a preceding detection area of a preceding image section in the acquisition direction. The detection area can optionally be determined along a diagonal of the detection zone. Otherwise, the strip-shaped detection area is formed parallel to an edge of the detection zone.

In the detecting step S6, the image section is detected by way of the determined detection area and the X-ray source.

In the generating step S7, a composite X-ray image of the region of interest is generated from the image sections.

In an optional determining step S8, a start and/or a stop position of the region of interest can be determined via a camera unit. This step can comprise automatic pinpointing of at least one landmark of the examinee. The landmark can be located via a neural network.

In an optional adjusting step S9, a first collimation of the X-ray source perpendicular to the acquisition direction can be set based on an image obtained by a camera unit, in particular automatically.

In an optional varying step S10, a second collimation of the X-ray source parallel to the acquisition direction can be varied or changed between successive image sections.

In an optional dose modulation step S11, dose modulation for lateral X-ray acquisition can be determined based on a previous frontal X-ray acquisition of the region of interest.

Figure 2:
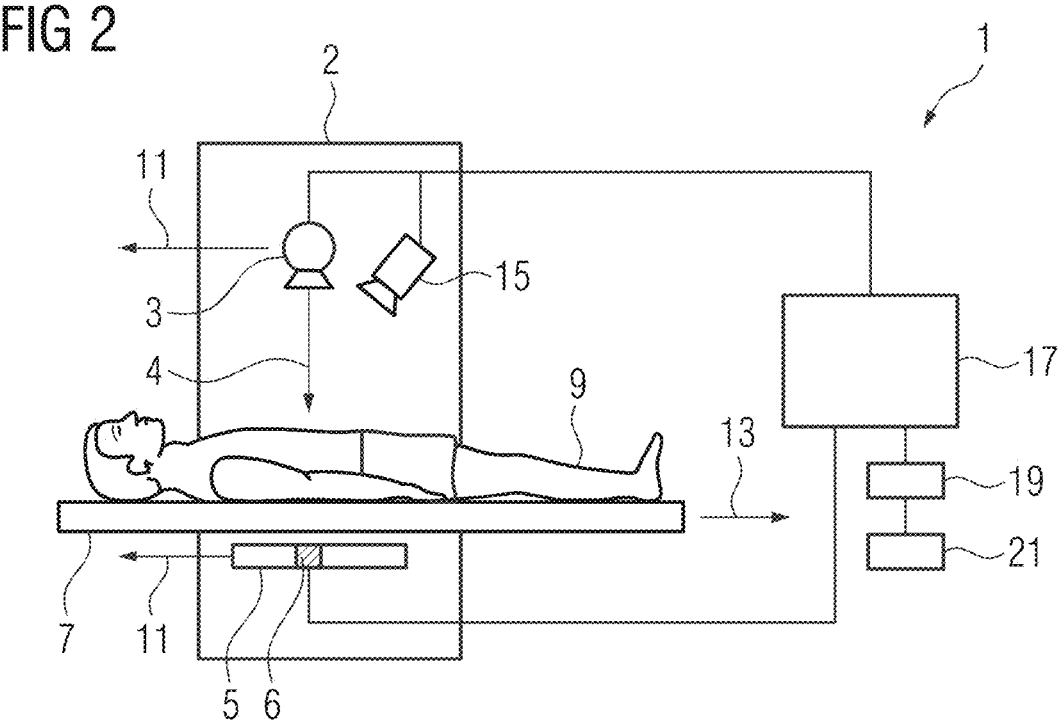
FIG. 2 schematically illustrates an X-ray system according to an embodiment of the invention.

FIG. 2 shows an example embodiment of an X-ray system 1 according to the invention, comprising an X-ray source 3 disposed on a traversing unit 2 and an X-ray detector 5 having a detection zone disposed on the traversing unit 2, and a displaceable patient table 7 for positioning the examinee 9. The X-ray source 3 and the X-ray detector 5 are in particular mechanically interconnected so that both can be moved in the acquisition direction 11 via an in particular common traversing unit 2. The patient table 7 can be moved in the opposite direction to the acquisition direction 13. The X-ray source 3 emits X-rays 4 to the detection area 6 within the detection zone. The X-rays 4 are collimated such that the size of the detection area is essentially determined thereby. The X-ray detector 5 can be read completely or limited to the detection area. The examinee 9 is disposed on the patient table 7 between the X-ray source 3 and the X-ray detector 5. The X-ray system 1 can additionally comprise a camera unit 15. The camera unit 15 can in particular be disposed close to the collimator on the X-ray source 3. The collimator can be designed to collimate an essentially rectangular field of X-rays, in particular by way of two pairs of diaphragms. The X-ray system 1 can further comprise a computer unit 17, a display unit 19 and an input unit 21.

Figure 3:
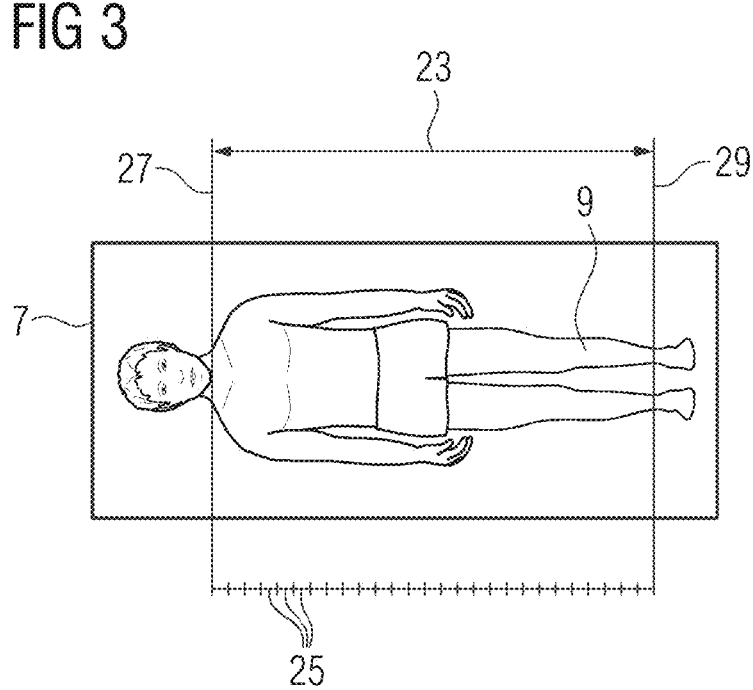
FIG. 3 schematically illustrates a region of interest according to an embodiment of the invention.

FIG. 3 shows an example embodiment of a region of interest 23 according to the invention. By way of example, the examinee/patient 9 is recumbent on the patient table 7. The region of interest 23 is delimited by the start position 27 and the stop position 29. The region of interest 23 is acquired using the image sections 25. The center position is indicated for each of the image sections 25. Adjacent image sections 25 overlap in such a way that a point of the region of interest 23 is covered by a plurality of image sections.

Figure 4:
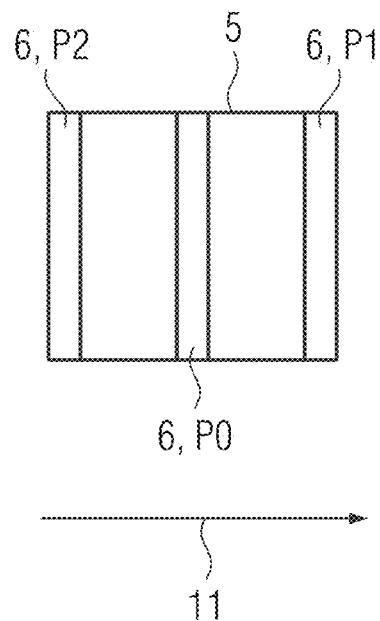
FIG. 4 schematically illustrates a first detection area according to an embodiment of the invention.

FIG. 4 shows an example embodiment of a first detection area 6 according to the invention at different positions P0, P1, P2 within the detection zone of the X-ray detector 5. For example, a first image section can be acquired with the detection area 6 in a central position P0. If the detection area 6 is displaced within the detection zone, the subsequent image section is acquired e.g. with the detection area 6 in the first position P1 and/or a previous image section is acquired with the detection area 6 in the second position P2. For example, the detection area 6 can move from the second position P2 to the central position P0 to the first position P1 along the acquisition direction 11. Alternatively, the detection area 6 can remain at a predetermined position, e.g. the central position P0, for a plurality of image sections.

Figure 5:
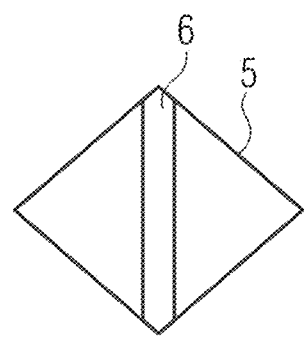
FIG. 5 schematically illustrates a second detection area according to an embodiment of the invention.
Figure 5:
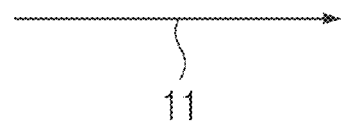

FIG. 5 shows an example embodiment of a first detection area 6 according to the invention along the diagonal of the detection zone. The detection area 6 is oriented perpendicular to the acquisition direction.

Although the invention has been illustrated in detail by the preferred example embodiment, the invention is not limited by the examples disclosed and other variations will be apparent to persons skilled in the art without departing from the scope of protection sought for the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for acquiring an X-ray image of a region of interest of an examinee using an X-ray system, the X-ray system including an X-ray source on a traversing unit, an X-ray detector on the traversing unit, and a displaceable patient table configured to position the examinee, the X-ray detector including a detection zone, and the method comprising:
selecting the region of interest;
acquiring, section-by-section, successive image sections in relation to the region of interest,
wherein the acquiring, for each successive image section of the successive image sections, includes
moving the X-ray source and the X-ray detector along an acquisition direction,
moving the displaceable patient table a same distance as the X-ray source and the X-ray detector in a direction counter to the acquisition direction,
determining a respective strip-shaped detection area within the detection zone for a respective image section of the successive image sections, and
detecting the respective image section by way of the respective strip-shaped detection area and the X-ray source, to acquire the respective image section; and
generating a composite X-ray image of the region of interest from the successive image sections.

2. The method of claim 1, wherein the moving the X-ray source and the X-ray detector, and the moving the displaceable patient table are performed simultaneously.

3. The method of claim 1, further comprising:
determining at least one of a start position or a stop position of the region of interest via a camera unit.

4. The method of claim 1, further comprising:
setting a first collimation of the X-ray source perpendicular to the acquisition direction based on an image obtained via a camera unit.

5. The method of claim 1, further comprising:
varying a collimation width of the X-ray between successive image sections, the collimation width parallel to the acquisition direction.

6. The method of claim 1, further comprising:
determining dose modulation for lateral X-ray acquisition, of the respective strip-shaped detection area, based on a previous frontal X-ray acquisition of the region of interest.

7. The method of claim 1, further comprising:
shifting the respective strip-shaped detection area, within the detection zone, in the acquisition direction compared to a respective preceding detection area of a respective preceding image section of the successive image sections.

8. The method of claim 1, wherein the determining the respective strip-shaped detection area includes determining the respective strip-shaped detection area along a diagonal of the detection zone.

9. A non-transitory computer-readable medium storing program sections, readable and executable by at least one processor at an X-ray system, for performing the method of claim 1 when the program sections are executed by the at least one processor.

10. The method of claim 1, wherein the moving the displaceable patient table includes moving the displaceable patient table such that a relative speed between the X-ray source and the displaceable patient table is between 200 and 300 mm/s.

11. The method of claim 2, further comprising:
determining at least one of a start position or a stop position of the region of interest via a camera unit.

12. The method of claim 2, further comprising:
setting a first collimation of the X-ray source perpendicular to the acquisition direction based on an image obtained via a camera unit.

13. A non-transitory computer-readable medium storing program sections, readable and executable by at least one processor at an X-ray system, for performing the method of claim 2 when the program sections are executed by the at least one processor.

14. The method as claimed in claim 3, further comprising:
automatically locating at least one landmark of the examinee.

15. The method as claimed in claim 14, further comprising:
pinpointing the landmark via a neural network.

16. The method as claimed in claim 11, further comprising:
automatically locating at least one landmark of the examinee.

17. The method as claimed in claim 16, further comprising:
pinpointing the landmark is via a neural network.

18. A medical X-ray system, comprising:
an X-ray source on a traversing unit;
an X-ray detector on the traversing unit, the X-ray detector including a detection zones;
a displaceable patient table configured to position and examinee; and
at least one processor configured to cause the medical X-ray system to select a region of interest,
  select a region of interest,
  acquire, section-by-section, successive image sections in relation to the region of interest by,
    moving the X-ray source and the X-ray detector along acquisition direction,
    moving the displaceable patient table a same distance as the X-ray source and the X-ray detector in a direction counter to the acquisition direction,
    determining a respective strip-shaped detection area within the detection zone for a respective image section of the successive image sections, and
    detecting the respective image section by way of the respective strip-shaped detection area and the X-ray source, to acquire the respective image section, and
  generate a composite X-ray image of the region of interest from the successive image sections.

* * * * *